Figure 1:
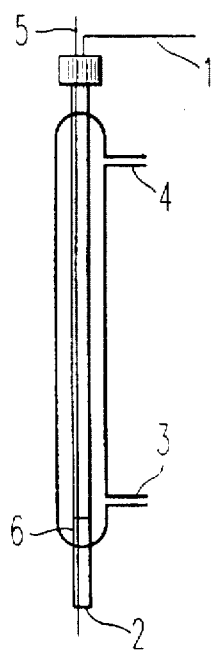

United States Patent [19]

Marchionna et al.

[11] Patent Number: 5,723,687
[45] Date of Patent: Mar. 3, 1998

[54] PROCESS FOR THE JOINT PRODUCTION OF ETHERS AND HYDROCARBONS WITH A HIGH OCTANE NUMBER

[75] Inventors: Mario Marchionna, Milan; Francesco Ancillotti, S. Donate Milanese; Marco Di Gerolamo, Melegnano, all of Italy

[73] Assignee: Snamprogetti S.p.A., Milan, Italy

[21] Appl. No.: 648,421

[22] Filed: May 15, 1996

[30] Foreign Application Priority Data

Jun. 1, 1995 [IT] Italy .................. MI 95/A1140

[51] Int. Cl.$^6$ .................................................. C07C 41/00
[52] U.S. Cl. ........................................ 568/697; 568/691
[58] Field of Search ............................. 568/697, 691

[56] References Cited

U.S. PATENT DOCUMENTS 4,571,439  2/1986  Keyworth .
4,950,803  8/1990  Smith et al. .................... 568/697

FOREIGN PATENT DOCUMENTS 0 008 860  3/1980  European Pat. Off. .
0 048 893  4/1982  European Pat. Off. .

*Primary Examiner*—C. Warren Ivy
*Assistant Examiner*—Sreeni Padmanabhan
*Attorney, Agent, or Firm*—Oblon, Spivak, McClelland, Maier & Neustadt, P.C.

[57] ABSTRACT

A process is described for the joint production of ethers and hydrocarbons with a high octane number starting from $C_4$ hydrocarbon cuts containing isobutene, by oligomerization with acid catalysts, in the presence of primary alcohols selected from methanol or ethanol in such a quantity as to have a molar ratio primary alcohols/isobutene in the feeding of between 0.2 and 0.7, preferably operating at a reaction temperature of between 30° and 100° C. and at feeding space velocities of less than 20 h$^{-1}$.

12 Claims, 1 Drawing Sheet

PROCESS FOR THE JOINT PRODUCTION OF ETHERS AND HYDROCARBONS WITH A HIGH OCTANE NUMBER

The present invention relates to a process for the joint production of ethers and hydrocarbons with a high octane number, obtained by the reaction of $C_4$ hydrocarbon cuts containing isobutene, with primary alcohols in stoichiometric defect with respect to the isobutene. The mixture obtained can then be optionally hydrogenated with the conventional methods to obtain a product with further improved octane characteristics.

For reasons of an environmental nature the composition of gasolines are being reformulated; the "Clean Air Act Amendments" (CAAA) in the USA are issuing general regulations which will probably also be adopted with few variations by other countries in the near future.

In short, the general tendency is towards the production of fuels which burn better and have fewer evaporation discharges. The main measures for reaching this objective are the following (for more specific details see for example: G. H. Unzelman, Fuel Reformulation, 31 (2), (1993), 41 and D. Sanfilippo, F. Ancillotti, M. Marchionna, Chim.&Ind., 76, (1994), 32 and references contained therein):

- oxygenated compounds will have a more and more important role as components of gasolines;
- the content of aromatic compounds will be considerably reduced, especially in gasolines;
- there will be a reduction in the volatility of gasolines to minimize the evaporative losses;
- the content of olefins, photochemically reactive and precursors responsible for the formation of atmospheric ozone, will be reduced;
- both the content of sulphur and the final boiling point of gasolines will also be reduced.

All these measures naturally create the necessity of inventing new processes capable of positively contributing to the above requirements.

With respect to the production of oxygenated products (or rather those which have proved to be most promising in this group) it should be noted that the CAAA have assigned a permanent function to these in the future reformulated gasolines both as raisers of the octane number and oxygen suppliers.

Ter-alkyl ethers have asserted themselves as preferred oxygenated compounds: among these the most important are MTBE (methyl-ter-butylether), ETBE (ethyl-ter-butylether) and TAME (ter-amyl-methylether). These ethers are generally obtained by the reaction in a liquid phase of $C_4$–$C_5$ iso-olefins with methanol or ethanol in the presence of an acid macromolecular resin with ion exchange. The production of these ethers, mainly MTBE, has been continually increasing in the last few years (for more specific details see for example: H. L. Brockwell, P. R. Sarathy, R. Trotta, Hydrocarbon Proc., September 1991, 133 and W. J. Piel, Fuel Reformulation, 2 (6), (1992), 34).

As well as oxygenated compounds, purely hydrocarbon products are also proving to be particularly attractive for the reformulation of gasolines; among these alkylate is particularly suitable as it has a high octane number, a low volatility and is practically without olefins and aromatics.

The alkylation processs in a liquid phase is a reaction between isoparaffinic hydrocarbons, such as isobutane, and olefins, for example propylene, butenes, pentenes and related mixtures, in the presence of an acid catalyst for the production of $C_7$–$C_9$ hydrocarbons with a high octane number to be used in gasolines (see for example: A. Corma, A. Martinez, Catal. Rev.-Sci. Eng., 35, (1993), 483 and references contained therein).

The main problem of the alkylation process is due to the fact that with the increasing number of environmental regulations both the traditional processes (with hydrofluoric acid and sulphuric acid), are encountering great difficulties which make their future uncertain; that with hydrofluoric acid owing to the toxicity of this acid, especially in populated areas, and the process with sulphuric acid owing to the high production of acid mud and to the considerably corrosive nature of the catalyst.

Alternative processes with solid acid catalysts are being developed but their commercial applicability still has to be proved.

On the other hand, a hydrocarbon product of this kind is always more desirable owing to its octanic characteristics (both the Research Octane Number (RON) and the Motor Octane Number (MON) are high) and those relating to the boiling point (limited volatility but low final point) which place it in the group of extremely interesting compositions for obtaining gasolines which are more compatible with present environmental demands.

In addition hydrocarbon products with a high octane number such as those generated by alkylation reaction also have a low sensitivity (difference between RON and MON) and it is known that ethers such as MTBE, ETBE, etc., react favourably to a lowering of the sensitivity of gasoline, further increasing their already high octance value.

This means that there are many advantages in coupling a saturated hydrocarbon product with a high octane number (such as alkylate) with ethers such as MTBE. In addition the joint presence of significant quantities of the two products also permits the content of undesirable components such as aromatics, olefins and sulphur, to be considerably reduced by dilution. In the past alternative proposals have been made for substituting alkylate with another product having a high octane number.

The joint production of oligomers of isobutene with MTBE, obtained by a two-step process, has in fact been disclosed (DE-2944457). In the first step the isobutene was oligomerized with conversions of between 50–90% to oligomers and then in a second step etherified with methanol to produce MTBE. A partial hydrogenation of the total product was also suggested.

The main problem of this process lies in the fact that in the oligomerization phase, heavy oligomers such as trimers and tetramers of isobutene are produced in excessive percentages (weight selectivity inside the fraction of oligomers of 15–30% and 1–2% respectively). The selectivity in the fraction of oligomers will always be given by weight in the text hereafter. Tetramers are completely excluded from the gasoline fraction as they are too high boiling and therefore produce a distinct loss in the gasoline yield; with respect to trimers (or their hydrogenated derivatives) is preferable to greatly reduce their concentration as they have a boiling point (170°–180° C.) which is on the limit of the future specifications for the final point of the reformulated gasolines.

On the other hand the problem of minimizing the formation of oligomers higher than dimers to lower percentages 10–15% is a problem which is typical of the oligomerization of isobutene as is also described in literature relating to both the processes for obtaining "polymer" gasoline and for those for intermediates of petrochemical interest (F. Asinger, "Mono-olefins: Chemistry and Technology", Pergamon Press, Oxford, pages 435–456 and G. Scharfe, Hydrocarbon Proc., April 1973, 171).

From the above it is evident that there is great interest in obtaining a new process for the dimerization of isobutene which allows the production of a higher quality product, in obtaining greater selectivities.

It is known that by carrying out the etherification reaction of $C_4$ iso-olefins in the presence of substoichiometric quantities of primary alcohols and operating with substoichiometric methanol/isobutene ratios, dimers of isobutene and MTBE can be formed (IT-1012690 of F. Ancillotti, G. Oriani, E. Pescarollo, F. Ancillotti, M. Massi Mauri, E. Pescarollo, L. Romagnoni, J. Mol. Catal., 4 (1978) 37).

The fact that by operating with substoichiometric ratios of methanol/isobutene it was possible to obtain much more controlled selectivities in dimers, within the fraction of oligomers, with respect to the dimerization/oligomerization of isobutene alone, emerged in one of the first patent applications on the application of the column reactor (EP-8860 of L. A. Smith Jr.). The same patent application claimed the production of fractions rich in di-isobutenes by the decomposition of MTBE; in a subsequent patent (U.S. Pat. No. 4,375,576 of L. A. Smith Jr) this invention was extended to the dimerizing/oligomerizing treatment of isobutene in the presence of varying quantities of MTBE.

In another patent application (EP-48893 of Kohler, H. D., Scheef H.-V., Schleppinghoff B.) a palladium-containing acid resin is used as catalyst (instead of a normal acid resin); it should be noted however that the use of palladium has no influence whatever in this type of process.

Other patents have been published on this subject (U.S. Pat. No. 4,950,803 of Smith Jr., L. A., Hearn, D., Jones Jr., E. M., EP-466954 of Smith Jr., L. a.).

It has now been found that there are ranges of the ratio primary alcohol/isobutene for which the co-production of ethers with a high octane number and a fraction of oligomers of the iso-olefin, rich in dimers and very poor in tetramers and higher oligomers, can be selectively obtained.

In addition, it has been surprisingly found that, depending on the composition of the particular $C_4$ charge, containing isobutene, and the type of primary alcohol with which the reaction is carried out, there are certain very limited ranges of the ratio primary alcohol/isobutene for which the co-production of ethers with a high octane number and a fraction of oligomers of the iso-olefin, particularly rich in dimers (selectivity >90%) and practically without tetramers and higher oligomers (<1%), are selectively obtained.

A further advantage of the present invention relates to the global process for the co-production of ethers and oligomers with a high octane number which can be much more easily controlled from a thermic point of view with respect to the single oligomerization process, thus greatly simplifying the problems of running the process itself.

The reaction product can then be hydrogenated to give a completely saturated final product with a high octane number and low sensitivity. The hydrogenation can be carried out with the conventional methods such as those described by F. Asinger in "Mono-olefins: Chemistry and Technology", Pergamon Press, Oxford, page 455.

As an example Table I below indicates the octane number of some of the products obtained with the process of the present invention:

TABLE I

| Product | RON | MON |
|---|---|---|
| MTBE | 118 | 100 |
| ETBE | 119 | 102 |

TABLE I-continued

| Product | RON | MON |
|---|---|---|
| TAME | 111 | 98 |
| di-isobutenes | 100 | 89 |
| iso-octane | 100 | 100 |
| tri-isobutenes | 100 | 89 |
| hydrogenated tri-isobutenes | 101 | 102 |

Optionally the hydrocarbon product (both olefinic and saturated) can also be separated from the ether fraction as it is higher boiling (at least in the case of products deriving from methanol and ethanol) and used separately from the ethers; operating as such however there is no longer the advantage deriving from a lowering of the sensitivity of the product, comprising both the oxygenated products and saturated hydrocarbons, mixed with a basic gasoline.

Table II shows a typical range of concentrations of the constituents of the mixture obtained by the co-production of the present invention. It should be pointed out however that in particular situations compositions outside of this range can also be accepted.

TABLE II

| Average composition of mixture | |
|---|---|
| Component | (%) by weight |
| Ether | 30–90 |
| $C_8$ hydrocarbons | 10–60 |
| $C_{12}$ hydrocarbons | 0.2–5 |
| $C_{16}$ hydrocarbons and higher | <0.5 |

The process of the present invention, for the joint production of ethers and hydrocarbons with a high octane number starting from $C_4$ hydrocarbon cuts containing isobutene, by oligomerization with acid catalysts, is characterized in that the oligomerization reaction is carried out in the presence of primary alcohols selected from methanol and ethanol in such a quantity as to have a molar ratio primary alcohols/isobutene in the feeding of between 0.2 and 0.7. The preferred molar ratio alcohol/isobutene strictly depends on the composition of the particular $C_4$ charge.

In this respect it should be noted that in the case of isobutene contained inside the $C_4$ hydrocarbon streams also comprising linear olefins, it has been observed that at least a part of the linear olefins can be converted into hydrocarbon product without jeopardizing the octane value. It is also preferable to carry out an enriching treatment, by pre-isomerization, of the internal olefins (2-butenes) inside the fraction of linear olefins, as the total octane number of the mixture has increased.

The object of the present invention can be applied to $C_4$ olefinic streams of different compositions. The relative streams will typically contain, inside the $C_4$ fraction, isobutane, isobutene, n-butane and n-butenes in differing proportions; although there is a wide variety of sources for supplying these streams, the most common are those deriving from dehydrogenation processes of iso-paraffins, from FCC units and streams coming from steam crackers.

Finally when these streams contain diolefins in addition to the desired mono-olefins, it will be necessary to eliminate them with the typical removal methods (for example washing or selective hydrogenation).

In addition to the hydrocarbon components the stream comprises the alcohol component (in stoichiometric defect) to produce the desired ether co-product.

The iso-olefin together with the hydrocarbon stream in which it is contained is sent with the alcohol (in stoichiometric defect) into contact with the acid catalyst to produce the ethers and higher oligomers of the iso-olefin. A wide variety of acid catalysts can be used for this process: among these, mineral acids can be cited, as an example, such as sulphuric acid, $BF_3$, supported phosphoric acid, zeolites appropriately modified, heteropolyacids and sulphonated polymeric resins, for example Amberlyst 15 and Amberlyst 35, etc. Among these catalysts the use of macroreticular sulphonated resins, generally copolymers of styrene and benzene, is preferred; the characteristics of these resins are widely described in literature (see for example A. Mitschker, R. Wagner, P. M. Lange, "Heterogeneous Catalysis and Fine Chemicals", M. Guisnet ed., Elsevier, Amsterdam, (1988), 61 and A. Chakrabarti, M. M. Sharma, React. Polym. 20 (1993), 1).

A wide range of operating conditions can be used for jointly producing ethers and hydrocarbons with a high octane number from primary alcohols and isobutene in the desired selectivity with the process of the present invention. It is possible to operate in a vapour phase or liquid-vapour phase but operating conditions in a liquid phase are preferred.

The process of the present invention can be carried out either batch-wise or in continuous, bearing in mind however that the latter is much more advantageous in industrial practice. The shape of the reactor can be optionally selected from a fixed bed reactor, tubular fixed bed, adiabatic, stirred and finally column reactor which also permits the separation of the products (a description of the different types of reactor generally used in industrial practice for the etherification process is provided for example in: P. R. Sarathy, G. S. Suffridge, Hydrocarbon Proc., February 1993, 45). Among these the tubular fixed bed reactor is considered preferable however owing to the possibility of removing the reaction heat (in extremely exothermic reactions such as that of the present invention). With this kind of reactor it is also possible to operate (with high reaction rates) at lower average temperatures than with other forms of reactor, thus allowing greater selectivities to be obtained in the desired products (dimers inside the fraction of oligomers).

The range of process conditions, operating in a liquid phase, comprises a wide variety of operating conditions which will be described hereafter.

The pressure is preferably superatmospheric to maintain the reagents in a liquid phase, generally below 5 MPa.

The reaction temperature is preferably between 30° and 100° C.

The feeding space velocities of the alcohol-hydrocarbon stream should be less than 20 $h^{-1}$, preferably between 1 and 10 $h^{-1}$.

The isobutene and primary alcohols are mainly converted in the reaction zone, however also part of the n-olefins can be converted to valuable product; generally there are no limits to the concentration of isobutene in the hydrocarbon fraction even if, to have significant productions of hydrocarbon product with high selectivities of dimers, it is preferable to have concentrations of between 10 and 60%, there are no limits in the ratio between isobutene and linear olefins. It should be noted that in the case of streams coming from the dehydrogenation of isobutane there are no linear butenes in the charge (see also Table III below).

The molar ratio selected between the alcohol fed and the iso-olefin must be substoichiometric with respect to the stoichiometric value of the etherification reaction, or between 0.2 and 0.7; it depends however on a large number of factors, such as:

the type of primary alcohol the conversion level of the isobutene the composition of the hydrocarbon charge the weight ratio oxygenated products/hydrocarbons to be obtained in the mixture produced.

It has generally been observed that the higher the ratio, the more selective is the production of dimers inside the hydrocarbon fraction of the product but the weight fraction of hydrocarbons with respect to the oxygenated products will be lower.

For ratios higher than 0.7, the production of dimers is generally very low with respect to that of the oxygenated products (<10% by weight), and consequently the upper limit of the molar ratio alcohol/isobutene should be about 0.7 to guarantee a sufficient production of hydrocarbon mixture.

The selectivity level of dimers to be reached cannot be univocally determined but in this case we will refer to minimum selectivities of 90%; in fact, an excessive percentage of higher oligomers jeopardizes the quality of the product, mainly due to the future reduction in the final point of the gasolines.

Referring therefore to minimum acceptable selectivities of 90% (obtained by conversions of isobutene of more than 75–80%), the preferred ratio alcohol/isobutene strictly depends on the type of alcohol and charge.

The charges basically consist of isobutene, n-butenes and $C_4$ saturates (n-butane and isobutane) and differ according to the varying relative concentrations.

When the charge consists of $C_4$ hydrocarbon cuts containing isobutene in a quantity of between 10 and 30% by weight and n-butenes in a quantity of between 25 and 50% by weight, it is advisable, to obtain better results, to operate depending on the selection of primary alcohol with a molar ratio methanol/isobutene of between 0.4 and 0.6 or with a molar ratio ethanol/isobutene of between 0.35 and 0.6 respectively.

When the charge consists of $C_4$ hydrocarbon cuts containing isobutene in a quantity of between 30 and 60% by weight, n-butenes in a quantity of more than 30% by weight and $C_4$ paraffins in a quantity of less than 15% by weight, it is advisable, to obtain better results, to operate depending on the primary alcohol selected with a molar ratio methanol/isobutene of between 0.25 and 0.6, in particular between 0.25 and 0.35, or with a molar ratio ethanol/isobutene of between 0.2 and 0.6, in particular between 0.2 and 0.35.

When the charge consists of $C_4$ hydrocarbon cuts containing isobutene in a quantity of between 28 and 60% by weight, $C_4$ paraffins in a quantity of more than 30% by weight and n-butenes in a quantity of less than 10% by weight, it is advisable, to obtain better results, to operate according to the primary alcohol selected with a molar ratio methanol/isobutene of between 0.45 and 0.6 or with a molar ratio ethanol/isobutene of between 0.4 and 0.6.

When the charge consists of $C_4$ hydrocarbon cuts containing isobutene in a percentage higher than 80% by weight, it is advisable, to obtain better results, to operate according to the selection of primary alcohol with a molar ratio methanol/isobutene of between 0.6 and 0.7 or with a molar ratio ethanol/isobutene of between 0.5 and 0.7.

Table III indicates the average compositions of typical $C_4$ hydrocarbon fractions coming from different sources (FCC, Steam Cracking, dehydrogenation of isobutane, isobutene streams with a high concentration).

TABLE III

| | Percentage compositions typical of $C_4$ streams | | | |
|---|---|---|---|---|
| | Steam Cracking | FCC | Dehydrogenation | Concentrated isobutene |
| Isobutene | 30–46 | 10–25 | 45–55 | >90 |
| n-butenes | 35–60 | 25–50 | | <10 |
| C4 saturates | 4–8 | 30–60 | 45–55 | <10 |

The following preferred ranges of the molar ratio alcohol/isobutene are shown in Table IV according to the type of alcohol and hydrocarbon charge.

TABLE IV

| | Preferred alcohol/isobutene molar ratios | | | |
|---|---|---|---|---|
| | Steam Cracking | FCC | Dehydrogenation | Concentrated isobutene |
| MeOH/ isobutene | 0.25–0.6 | 0.40–0.60 | 0.45–0.6 | 0.6–0.7 |
| EtOH/ isobutene | 0.20–0.6 | 0.35–0.60 | 0.40–0.6 | 0.5–0.7 |

For charges which are different from those generally available in industrial practice it should be noted that the addition of significant quantities of linear olefins with respect to the compositions of the charges mentioned above causes a slight rise in the selectivity of dimers and consequently a limited reduction (not more than 0.05 points) in the lower limit of the molar ratio alcohol/isobutene previously indicated. On the contrary, an increase in the content of saturated hydrocarbons causes a slight deterioration in the selectivity and consequently the value of the lower limit of the ratio is increased by not more than 0.05 points.

The process effluent is then sent to a separation zone where the primary alcohol, the non-reacted olefins and saturated $C_4$ hydrocarbons are separated from the reaction products. Various types of equipment can be used for this separation, among which also a column reactor.

As the conversion of the alcohol is always very high under the typical process conditions of the present invention, separation techniques can be used for the complete removal of the primary alcohol, which are typical of modern etherification technologies (exploiting the formation of azeotropic mixtures between the alcohol and $C_4$ hydrocarbon stream).

Finally, if total conversions of isobutene are not reached in the reactor wherein the joint production of ether and hydrocarbons with a high octane number takes place, depending on the particular use of the unconverted stream of $C_4$ hydrocarbons, the effluent separated at the head can also be optionally sent to a second etherification reactor, as is normally the case in modern technologies for the production of ter-alkyl ethers (P. R. Sarathy, G. S. Suffridge, Hydrocarbon Proc., February 1993, 45). This reactor may again be of a different form (adiabatic, column reactor or any other type which is considered suitable for the specific application).

The reaction product leaving this finishing reactor may then be optionally combined with that obtained in the first reactor.

The following examples provide a better understanding of the presnt invention but do not limit it in any way.

EXAMPLE 1

This example illustrates the use of the process of the present invention in a jacketed tubular reactor of which a drawing is shown in FIG. 1, with the following indications:

1-liquid inlet
2-liquid outlet
3-thermostat-regulated liquid inlet
4-thermostat-regulated liquid outlet
5-thermocouple
6-porous septum (of 100µ).

20 cc of resin with cation exchange, functionalized with sulphonic groups, Amberlyst 15 were charged into this stainless steel reactor, with an internal diameter of 1.4 cm and equipped with valves for the inlet of the reagents and outlet of the products.

The reaction heat which developed from the two exothermic reactions, was removed by the circulation of a cooling fluid (water at 40° C.) in the reactor jacket.

Figure 2:
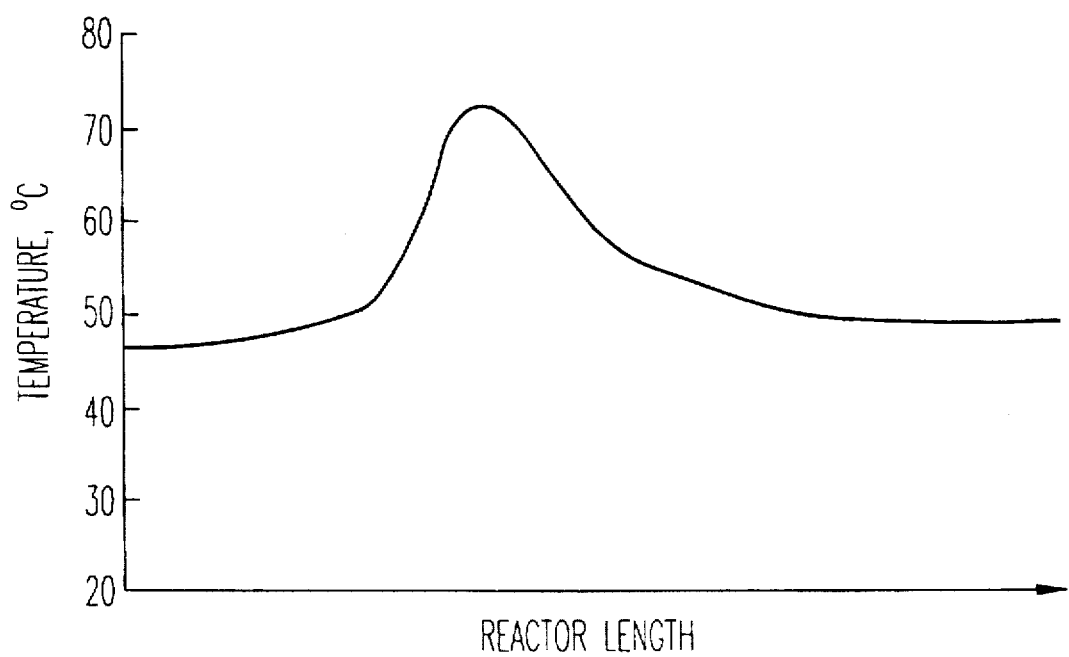

The thermal profile (an indicative one is shown in FIG. 2, where the length of the reactor is represented in abscissa and the temperature in ordinate) obtained by the process of the present invention showed in all the tests carried out a maximum temperature in the first third of the catalytic bed where the reaction rate is the highest.

A constant pressure of 1.5 MPa was maintained in the reactor, sufficient to keep the reagents liquid.

In this test methanol was used as primary alcohol and as a stream, a mixture of $C_4$ hydrocarbons with a composition similar to that leaving a dehydrogentation plant of isobutane (isobutene 48% by weight, isobutane 52% by weight). The feeding mixture, in which the molar ratio methanol/isobutene is 0.6, was sent to the reactor at a rate of 2 cc/min so as to have an LHSV space velocity of 6 volumes/hour per volume of catalyst (6 $h^{-1}$).

Operating under these conditions it was possible to obtain (once the equilibrium state had been reached) average conversions of methanol and isobutene of 98 and 78% respectively and a selectivity to dimers of 92%.

The maximum temperature reached in the reactor was 72° C.

In the equilibrium state, reached under the present conditions in less than 0.5 h, a product was obtained with the following composition:

| MTBE | 83.40% by weight |
|---|---|
| $C_8$ HYDROCARBONS | 15.34% by weight |
| $C_{12}$ HYDROCARBONS | 1.19% by weight |
| $C_{16 + HIGHER}$ HYDROCARBONS | 0.07% by weight |

EXAMPLE 2 (COMPARATIVE)

This example shows that if the reaction is carried out without primary alcohols it is not possible to limit the formation of heavy oligomers.

This test was carried out with the same equipment and under the same operating conditions described in example 1.

In this example a charge of the hydrocarbon type only was used, similar to a stream leaving a dehydrogenation plant of isobutane (isobutane 51% by weight and isobutene 49% by weight).

Without alcohol it is much more difficult to control the temperature inside the reactor (Tmax=90°–100° C.).

Also in this case very high conversions of isobutene were obtained (85%) but the selectivities to dimers were very low (55%).

In the equilibrium state, a product was obtained having the following composition:

| C₈ HYDROCARBONS | 55.20% by weight |
|---|---|
| C₁₂ HYDROCARBONS | 39.45% by weight |
| C₁₆ ₊ ₕᵢ₉ₕₑᵣ HYDROCARBONS | 5.35% by weight |

EXAMPLE 3

This example shows how also other resins with ion exchange are active in the process of the present invention.

Also in this case the equipment described in example 1 was used, using as catalyst however 20 cc of resin with cation exchange, functionalized with sulphonic groups, Amberlyst 15.

In addition, this test was carried out with a molar ratio methanol/isobutene of 0.4 and a hydrocarbon charge composed of isobutane (53% by weight) and isobutene (47% by weight). This mixture was fed to the reactor at a rate of 2 cc/min in order to have a space velocity of 6 volumes/hour per volume of catalyst.

Operating under these conditions it was possible to obtain average conversions of methanol and isobutene of 99 and 82% respectively, with a selectivity to dimers of 90%.

The maximum temperature reached in the reactor was 76° C.

In the equilibrium state, a product was obtained having the following composition:

| MTBE | 64.77% by weight |
|---|---|
| C₈ HYDROCARBONS | 31.73% by weight |
| C₁₂ HYDROCARBONS | 3.39% by weight |
| C₁₆ ₊ ₕᵢ₉ₕₑᵣ HYDROCARBONS | 0.11% by weight |

EXAMPLE 4

This example shows how, by varying the alcohol/isobutene ratio outside the advised ranges, an excessive formation of heavy oligomers is obtained.

This test was carried out with the same equipment and under the same operating conditions described in example 3 using a molar ratio MeOH/isobutene of 0.2.

Operating under these conditions it was possible to obtain average conversions of isobutene of 94%, with a selectivity to dimers of 75%.

The maximum temperature reached in the reactor was 76° C.

In the equilibrium state, a product was obtained having the following composition:

| MTBE | 29.98% by weight |
|---|---|
| C₈ HYDROCARBONS | 53.05% by weight |
| C₁₂ HYDROCARBONS | 16.12% by weight |
| C₁₆ ₊ ₕᵢ₉ₕₑᵣ HYDROCARBONS | 0.85% by weight |

EXAMPLE 5

This example shows how the presence of linear olefins (2-butene) in the hydrocarbon charge hardly modifies the reaction rate and selectivity to dimers of the process of the present invention.

This test was carried out using the same equipment and under the same operating conditions described in example 3 using a molar ratio MeOH/isobutene of 0.4. In this case however a $C_4$ hydrocarbon stream was used with a composition similar to that leaving an FCC unit, after the isomerization of 1-butene to 2-butene. The composition of the $C_4$ cut fed was therefore the following: isobutane 28% by weight, isobutene 23% by weight, 2-butene 49% by weight.

Under these conditions it was possible to obtain average conversions of methanol and isobutene of 99 and 86% respectively, with a selectivity to dimers (and codimers) of 90%.

The maximum temperature reached in the reactor was 60° C.

In the equilibrium state, a product was obtained having the following composition:

| MTBE | 57.34% by weight |
|---|---|
| C₈ DIMERS | 32.70% by weight |
| C₈ CODIMERS | 5.64% by weight |
| C₁₂ HYDROCARBONS | 4.16% by weight |
| C₁₆ ₊ ₕᵢ₉ₕₑᵣ HYDROCARBONS | 0.16% by weight |

The presence of codimers between isobutene and 2-butene does not deteriorate the quality of the product as these hydrocarbons, once hydrogenated, have octanic characteristics (RON and MON) similar to those of iso-octane.

EXAMPLE 6

This example shows the progress of the reaction with methanol and $C_4$ charges with different compositions. In this case a $C_4$ hydrocarbon stream was used coming from a Steam Cracking unit. The composition of the $C_4$ cut fed was therefore the following: isobutane 1% by weight, n-butane 4% by weight, isobutene 38% by weight, 1-butene 41% by weight, 2-butene 15% by weight, other products 1% by weight.

This test was carried out with the same equipment and under the same operating conditions described in example 3; the molar ratio MeOH/isobutene is 0.45.

Under these conditions it was possible to obtain average conversions of methanol and isobutene of 99 and 86% respectively, with a selectivity to dimers (and codimers) of 93%.

The maximum temperature reached in the reactor was 72° C.

In the equilibrium state, a product was obtained having the following composition:

| MTBE | 62.22% by weight |
|---|---|
| C₈ DIMERS | 27.68% by weight |
| C₈ CODIMERS | 7.54% by weight |
| C₁₂ HYDROCARBONS | 2.51% by weight |
| C₁₆ ₊ ₕᵢ₉ₕₑᵣ HYDROCARBONS | 0.05% by weight |

EXAMPLE 7

This example shows the progression of the reaction with methanol and a $C_4$ hydrocarbon stream coming from a Steam Cracking unit, using even lower molar ratios MeOH/isobutene (MeOH/isobutene=0.31).

This test was carried out with the same equipment and under the same operating conditions described in example 6.

Under these conditions it was possible to obtain average conversions of methanol and isobutene of 99 and 90% respectively, with a selectivity to dimers (and codimers) of 91%.

The maximum temperature reached in the reactor was 71° C.

In the equilibrium state, a product was obtained having the following composition:

| MTBE | 42.35% by weight |
|---|---|
| $C_8$ DIMERS | 44.28% by weight |
| $C_8$ CODIMERS | 8.19% by weight |
| $C_{12}$ HYDROCARBONS | 4.78% by weight |
| $C_{16 + HIGHER}$ HYDROCARBONS | 0.40% by weight |

EXAMPLE 8

This example shows the progress of the reaction with methanol and with $C_4$ loads of different compositions. In this case a $C_4$ hydrocarbon stream was used which was very rich in isobutene (isobutene: 95% by weight; 2-butene: 5% by weight).

This test was carried out with the same equipment and under the same operating conditions as example 3, but the feeding mixture, in which the molar ratio methanol/isobutene is 0.6, was sent to the reactor at a rate of 1 cc/min in order to have an LHSV space velocity of 3 volumes/hour per volume of catalyst (3 $h^{-1}$); in addition the temperature of the therostat-regulated water was 30° C.

Under these conditions it was possible to obtain average conversions of methanol and isobutene of 99 and 87% respectively, with a selectivity to dimers (and codimers) of 91%.

The maximum temperature reached in the reactor was 65° C.

In the equilibrium state, a product was obtained having the following composition:

| MTBE | 78.09% by weight |
|---|---|
| $C_8$ DIMERS | 19.98% by weight |
| $C_{12}$ HYDROCARBONS | 1.82% by weight |
| $C_{16 + HIGHER}$ HYDROCARBONS | 0.11% by weight |

EXAMPLE 9

This example shows how the process of the present invention can also be extended to higher primary alcohols such as ethanol.

This test was carried out with the same equipment and under the same operating conditions as example 3 using a molar ratio EtOH/isobutene of 0.435. Under these conditions it was possible to obtain average conversions of ethanol and isobutene of 98 and 85% respectively, with a selectivity to dimers of 92%.

The maximum temperature reached in the reactor was 73° C.

In the equilibrium state, a product was obtained having the following composition:

| ETBE | 65.7% by weight |
|---|---|
| $C_8$ HYDROCARBONS | 31.4% by weight |
| $C_{12}$ HYDROCARBONS | 2.7% by weight |
| $C_{16 + HIGHER}$ HYDROCARBONS | 0.2% by weight |

EXAMPLE 10

This example shows how, by varying the ethanol/isobutene ratio outside the advised ranges, an excessive formation of heavy oligomers is obtained.

This test was carried out with the same equipment and under the same operating conditions as example 9, but with a ratio EtOH/isobutene of 0.24. Under these conditions it was possible to obtain average conversions of ethanol and isobutene of 96 and 90% respectively, with a selectivity to dimers of 85%.

The maximum temperature reached in the reactor was 72° C.

In the equilibrium state, a product was obtained having the following composition:

| ETBE | 39.15% by weight |
|---|---|
| $C_8$ HYDROCARBONS | 52.23% by weight |
| $C_{12}$ HYDROCARBONS | 8.21% by weight |
| $C_{16 + HIGHER}$ HYDROCARBONS | 0.41% by weight |

EXAMPLE 11

This example shows the progression of the reaction with ethanol and $C_4$ charges with different compositions. In this case a $C_4$ hydrocarbon stream was used coming from a Steam Cracking unit. The composition of the $C_4$ cut fed was therefore the following: isobutane 1% by weight, n-butane 4% by weight, isobutene 38% by weight, 1-butene 41% by weight, 2-butene 15% by weight, other products 1% by weight.

This test was carried out with the same equipment and under the same operating conditions as example 9, but with a ratio EtOH/isobutene of 0.27.

Under these conditions it was possible to obtain average conversions of ethanol and isobutene of 98 and 87% respectively, with a selectivity to dimers (and codimers) of 91%.

The maximum temperature reached in the reactor was 69° C.

In the equilibrium state, a product was obtained having the following composition:

| ETBE | 44.17% by weight |
|---|---|
| $C_8$ DIMERS | 40.99% by weight |
| $C_8$ CODIMERS | 9.80% by weight |
| $C_{12}$ HYDROCARBONS | 4.84% by weight |
| $C_{16 + HIGHER}$ HYDROCARBONS | 0.20% by weight |

We claim:

1. Process for the joint production of ethers and hydrocarbons with a high octane number starting from a charge consisting of hydrocarbon cuts containing isobutene, by oligomerization with acid catalysts comprising carrying out the oligomerization reaction in the presence of one or more primary alcohols selected from methanol and ethanol in such a quantity as to have a molar ratio primary alcohols/isobutene in the feeding of between 0.2 and 0.7, operating at a reaction temperature of between 30° and 100° C., at a pressure of less than 5 Mpa and at a feeding space velocity of less than 20 $h^{-1}$.

2. Process according to claim 1 wherein the charge consists of $C_4$ hydrocarbon cuts containing isobutene in a quantity of between 10 and 30% by weight and n-butenes in a quantity of between 25 and 50% by weight and the molar ratio methanol/isobutene is between 0.4 and 0.6.

3. Process according to claim 1 wherein the charge consists of $C_4$ hydrocarbon cuts containing isobutene in a quantity of between 10 and 30% by weight and n-butenes in a quantity of between 25 and 50% by weight and the molar ratio ethanol/isobutene is between 0.35 and 0.6.

4. Process according to claim 1 wherein the charge consists of $C_4$ hydrocarbon cuts containing isobutene in a quantity of between 30 and 60% by weight, n-butenes in a quantity of more than 30% by weight and $C_4$ paraffins in a quantity of less than 15% by weight and the molar ratio methanol/isobutene is between 0.25 and 0.6.

5. Process according to claim 4 wherein the molar ratio methanol/isobutene is between 0.25 and 0.35.

6. Process according to claim 1 wherein the charge consists of $C_4$ hydrocarbon cuts containing isobutene in a quantity of between 30 and 60% by weight, n-butenes in a quantity of more than 30% by weight and $C_4$ paraffins in quantities of less than 15% by weight and the molar ratio ethanol/isobutene is between 0.2 and 0.6.

7. Process according to claim 6 wherein the molar ratio ethanol/isobutene is between 0.2 and 0.35.

8. Process according to claim 1 wherein the charge consists of $C_4$ hydrocarbon cuts containing isobutene in a quantity of between 30 and 60%, $C_4$ paraffins in a quantity of more than 30% by weight and n-butenes in quantities of less than 10% by weight and the molar ratio methanol/isobutene is between 0.45 and 0.6.

9. Process according to claim 1 wherein the charge consists of $C_4$ hydrocarbon cuts containing isobutene in a quantity of between 30 and 60%, $C_4$ paraffins in a quantity of more than 30% by weight and n-butenes in quantities of less than 10% by weight and the molar ratio ethanol/isobutene is between 0.4 and 0.6.

10. Process according to claim 1 wherein the charge consists of $C_4$ hydrocarbon cuts containing isobutene in quantities of more than 80% by weight and the molar ratio methanol/isobutene is between 0.6 and 0.7.

11. Process according to claim 1 wherein the charge consists of $C_4$ hydrocarbon cuts containing isobutene in quantities of more than 80% by weight and the molar ratio ethanol/isobutene is between 0.5 and 0.7.

12. Process according to any of the claims from 1 to 11 wherein the feeding space velocities are between 1 and 10 $h^{-1}$.

* * * * *